(12) United States Patent
Davison et al.

(10) Patent No.: US 8,870,864 B2
(45) Date of Patent: Oct. 28, 2014

(54) SINGLE INSTRUMENT ELECTROSURGERY APPARATUS AND ITS METHOD OF USE

(75) Inventors: Paul O. Davison, Montara, CA (US); Ralph I. McNall, III, Menlo Park, CA (US); John R. Tighe, Los Gatos, CA (US); Alexander B. Vankov, Menlo Park, CA (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 567 days.

(21) Appl. No.: 13/284,621

(22) Filed: Oct. 28, 2011

(65) Prior Publication Data
US 2013/0110108 A1 May 2, 2013

(51) Int. Cl.
*A61B 18/00* (2006.01)
*A61B 18/14* (2006.01)

(52) U.S. Cl.
CPC ..... *A61B 18/1402* (2013.01); *A61B 2018/1495* (2013.01); *A61B 2018/00589* (2013.01); *A61B 2018/00565* (2013.01); *A61B 2018/00601* (2013.01)
USPC .................................. 606/41; 606/46; 606/49

(58) Field of Classification Search
None
See application file for complete search history.

(56) References Cited

U.S. PATENT DOCUMENTS

| | | |
|---|---|---|
| 2,888,928 A | 6/1959 | Seiger |
| 3,682,130 A | 8/1972 | Jeffers |
| 3,750,650 A | 8/1973 | Ruttgers |
| 4,014,343 A * | 3/1977 | Esty .................. 606/45 |
| 4,060,088 A | 11/1977 | Morrison, Jr. et al. |
| 4,074,718 A | 2/1978 | Morrison, Jr. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |

(Continued)

FOREIGN PATENT DOCUMENTS

| | | |
|---|---|---|
| EP | 0 830 846 A1 | 3/1998 |
| EP | 0 830 846 B1 | 3/1998 |

(Continued)

OTHER PUBLICATIONS

Wikipedia (Nov. 21, 2010). "Diamond-like carbon," located at <http://en.wikipedia.org/wiki/Diamond-like_carbon> last visited on Apr. 6, 2011, six pages.

*Primary Examiner* — Brian T Gedeon
(74) *Attorney, Agent, or Firm* — Jeffrey J. Hohenshell (57) ABSTRACT

An electrosurgical apparatus includes two assemblies, one of which is the primary assembly intended for a first surgical procedure, such as cutting tissue, and a secondary assembly intended for a second type of electrosurgical procedure, such as tissue coagulation. The secondary assembly fits over the electrode tip of the primary assembly and makes electrical contact with the electrode tip of the primary assembly. This allows for single instrument surgery whereby the secondary (coagulation) assembly provides bleeding control after the primary assembly has cut tissue. This combination significantly reduces operating time. The secondary assembly has a snap fit over the primary assembly so that it may be readily attached and detached several times during any surgical procedure, as the surgeon alternates between cutting tissue and coagulating the resulting incisions using the apparatus.

15 Claims, 5 Drawing Sheets

(56) References Cited

U.S. PATENT DOCUMENTS

| | | | |
|---|---|---|---|
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,936,281 A | 6/1990 | Stasz |
| 4,943,290 A | 7/1990 | Rexroth et al. |
| 4,946,460 A | 8/1990 | Merry et al. |
| 4,950,232 A | 8/1990 | Ruzicka et al. |
| 4,985,030 A | 1/1991 | Melzer et al. |
| 4,998,933 A | 3/1991 | Eggers et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,190,541 A | 3/1993 | Abele et al. |
| 5,195,959 A | 3/1993 | Smith |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,234,428 A | 8/1993 | Kaufman |
| 5,250,047 A | 10/1993 | Rydell |
| 5,254,116 A | 10/1993 | Baust et al. |
| 5,254,117 A | 10/1993 | Rigby et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,442 A | 12/1995 | Klicek |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,916 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |

(56) References Cited

U.S. PATENT DOCUMENTS

| | | | |
|---|---|---|---|
| 5,658,278 A | 8/1997 | Imran et al. | |
| 5,662,647 A | 9/1997 | Crow et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | Lafontaine | |
| 5,678,550 A | 10/1997 | Bassen et al. | |
| 5,680,860 A | 10/1997 | Imran | |
| 5,681,278 A | 10/1997 | Igo et al. | |
| 5,681,294 A | 10/1997 | Osborne et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | |
| 5,697,536 A | 12/1997 | Eggers et al. | |
| 5,697,882 A | 12/1997 | Eggers et al. | |
| 5,697,925 A | 12/1997 | Taylor | |
| 5,697,927 A | 12/1997 | Imran et al. | |
| 5,697,928 A | 12/1997 | Walcott et al. | |
| 5,713,942 A | 2/1998 | Stern | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,718,719 A | 2/1998 | Clare et al. | |
| 5,720,775 A | 2/1998 | Lanard | |
| 5,722,402 A | 3/1998 | Swanson et al. | |
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | |
| 5,735,280 A | 4/1998 | Sherman et al. | |
| 5,735,290 A | 4/1998 | Sterman et al. | |
| 5,743,903 A | 4/1998 | Stern et al. | |
| 5,755,760 A | 5/1998 | Maguire et al. | |
| 5,766,167 A | 6/1998 | Eggers et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,905 A | 8/1998 | Fleischman et al. | |
| 5,797,960 A | 8/1998 | Stevens et al. | |
| 5,800,428 A | 9/1998 | Nelson et al. | |
| 5,800,482 A | 9/1998 | Pomeranz et al. | |
| 5,810,764 A | 9/1998 | Eggers et al. | |
| 5,810,802 A | 9/1998 | Panescu et al. | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,843,021 A | 12/1998 | Edwards et al. | |
| 5,843,152 A | 12/1998 | Tu et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,861,021 A | 1/1999 | Thome et al. | |
| 5,871,523 A | 2/1999 | Fleischman et al. | |
| 5,871,525 A | 2/1999 | Edwards et al. | |
| 5,873,845 A | 2/1999 | Cline et al. | |
| 5,873,855 A | 2/1999 | Eggers et al. | |
| 5,876,399 A | 3/1999 | Chia et al. | |
| 5,879,295 A | 3/1999 | Li et al. | |
| 5,879,296 A | 3/1999 | Ockuly et al. | |
| 5,879,348 A | 3/1999 | Owens et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,891,142 A | 4/1999 | Eggers et al. | |
| 5,893,848 A | 4/1999 | Negus et al. | |
| 5,895,355 A | 4/1999 | Schaer | |
| 5,895,417 A | 4/1999 | Pomeranz et al. | |
| 5,897,553 A | 4/1999 | Mulier | |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,908,029 A | 6/1999 | Knudson et al. | |
| 5,913,854 A | 6/1999 | Maguire et al. | |
| 5,916,213 A | 6/1999 | Haissaguerre et al. | |
| 5,916,214 A | 6/1999 | Cosio et al. | |
| 5,921,924 A | 7/1999 | Avitall | |
| 5,921,982 A | 7/1999 | Lesh et al. | |
| 5,925,045 A | 7/1999 | Reimels et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,935,123 A | 8/1999 | Edwards et al. | |
| 5,944,715 A | 8/1999 | Goble et al. | |
| 5,954,661 A | 9/1999 | Greenspon et al. | |
| 5,957,919 A | 9/1999 | Laufer | |
| 5,971,980 A | 10/1999 | Sherman | |
| 5,971,983 A | 10/1999 | Lesh | |
| 5,980,516 A | 11/1999 | Mulier et al. | |
| 5,984,918 A | 11/1999 | Garito et al. | |
| 5,989,248 A | 11/1999 | Tu et al. | |
| 5,993,412 A | 11/1999 | Deily et al. | |
| 5,993,447 A | 11/1999 | Blewett et al. | |
| 6,004,316 A | 12/1999 | Laufer | |
| 6,004,319 A | 12/1999 | Goble et al. | |
| 6,007,499 A | 12/1999 | Martin et al. | |
| 6,010,500 A | 1/2000 | Sherman et al. | |
| 6,012,457 A | 1/2000 | Lesh | |
| 6,015,391 A | 1/2000 | Rishton et al. | |
| 6,016,811 A | 1/2000 | Knopp et al. | |
| 6,018,676 A | 1/2000 | Davis et al. | |
| 6,019,757 A | 2/2000 | Scheldrup | |
| 6,024,733 A | 2/2000 | Eggers et al. | |
| 6,030,381 A | 2/2000 | Jones et al. | |
| 6,036,687 A | 3/2000 | Laufer et al. | |
| 6,042,556 A | 3/2000 | Beach et al. | |
| 6,048,333 A | 4/2000 | Lennox et al. | |
| 6,056,744 A | 5/2000 | Edwards | |
| 6,056,745 A | 5/2000 | Panescu et al. | |
| 6,056,746 A | 5/2000 | Goble | |
| 6,056,747 A | 5/2000 | Saadat et al. | |
| 6,063,081 A | 5/2000 | Mulier | |
| 6,066,139 A | 5/2000 | Ryan et al. | |
| 6,068,653 A | 5/2000 | LaFontaine | |
| 6,071,279 A | 6/2000 | Whayne et al. | |
| 6,074,386 A | 6/2000 | Goble et al. | |
| 6,083,237 A | 7/2000 | Huitema et al. | |
| 6,086,585 A | 7/2000 | Hovda et al. | |
| 6,088,894 A | 7/2000 | Oakley | |
| 6,096,037 A | 8/2000 | Mulier | |
| 6,113,592 A | 9/2000 | Taylor | |
| 6,113,596 A | 9/2000 | Hooven et al. | |
| 6,117,101 A | 9/2000 | Diederich et al. | |
| 6,120,496 A | 9/2000 | Whayne et al. | |
| 6,141,576 A | 10/2000 | Littmann et al. | |
| 6,142,993 A | 11/2000 | Whayne et al. | |
| 6,142,994 A | 11/2000 | Swanson et al. | |
| 6,149,620 A | 11/2000 | Baker et al. | |
| 6,152,920 A | 11/2000 | Thompson et al. | |
| 6,161,543 A | 12/2000 | Cox et al. | |
| 6,165,174 A | 12/2000 | Jacobs et al. | |
| 6,190,384 B1 | 2/2001 | Ouchi | |
| 6,193,716 B1 | 2/2001 | Shannon, Jr. | |
| 6,210,406 B1 | 4/2001 | Webster | |
| 6,210,410 B1 | 4/2001 | Farin et al. | |
| 6,210,411 B1 | 4/2001 | Hofmann et al. | |
| 6,212,426 B1 | 4/2001 | Swanson | |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,231,591 B1 | 5/2001 | Desai | |
| 6,235,020 B1 | 5/2001 | Cheng et al. | |

(56) References Cited

U.S. PATENT DOCUMENTS

| | | |
|---|---|---|
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,558,385 B1 | 5/2003 | McClurken et al. |
| 6,565,561 B1 * | 5/2003 | Goble et al. ............ 606/41 |
| 5,697,536 C1 | 6/2003 | Eggers et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,057 B1 | 8/2003 | Ellman et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,115,139 B2 | 10/2006 | McClurken et al. |
| 7,156,845 B2 | 1/2007 | Mulier et al. |
| 7,166,106 B2 | 1/2007 | Bartel et al. |
| 7,198,625 B1 | 4/2007 | Hui et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | McClurken et al. |
| 7,625,347 B2 | 12/2009 | Burbank et al. |
| 7,645,277 B2 | 1/2010 | McClurken et al. |
| 7,651,494 B2 | 1/2010 | McClurken et al. |
| 7,736,361 B2 | 6/2010 | Palanker |
| 7,789,879 B2 | 9/2010 | Palanker et al. |
| 7,811,282 B2 | 10/2010 | McClurken |
| 7,815,634 B2 | 10/2010 | McClurken et al. |
| 7,909,820 B2 | 3/2011 | Lipson et al. |
| 7,942,872 B2 | 5/2011 | Ein-Gal |

(56) References Cited

U.S. PATENT DOCUMENTS

| | | |
|---|---|---|
| 7,976,544 B2 | 7/2011 | McClurken |
| 7,998,140 B2 | 8/2011 | McClurken |
| 8,038,670 B2 | 10/2011 | McClurken |
| 8,048,070 B2 | 11/2011 | O'Brien |
| 8,080,009 B2 | 12/2011 | Lee et al. |
| 8,083,736 B2 | 12/2011 | McClurken et al. |
| 8,105,323 B2 | 1/2012 | Buysse et al. |
| 8,177,783 B2 | 5/2012 | Davison et al. |
| 2002/0049483 A1 | 4/2002 | Knowlton |
| 2002/0062131 A1 | 5/2002 | Gallo, Sr. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0181904 A1* | 9/2003 | Levine et al. .................. 606/45 |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Shankey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0096646 A1* | 5/2005 | Wellman et al. ................ 606/41 |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0064085 A1 | 3/2006 | Schechter et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0071270 A1 | 3/2008 | Desinger et al. |
| 2008/0207028 A1 | 8/2008 | Schutz |
| 2009/0264879 A1 | 10/2009 | McClurken et al. |
| 2009/0306655 A1 | 12/2009 | Stangeness |
| 2010/0100095 A1 | 4/2010 | McClurken et al. |
| 2011/0028965 A1 | 2/2011 | McClurken |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0101496 A1 | 4/2012 | McClurken et al. |
| 2012/0116397 A1 | 5/2012 | Rencher et al. |
| 2012/0150165 A1 | 6/2012 | Conley et al. |
| 2012/0253343 A1 | 10/2012 | McClurken et al. |

FOREIGN PATENT DOCUMENTS

| | | |
|---|---|---|
| EP | 1 674 039 A2 | 6/2006 |
| EP | 1 674 039 A3 | 6/2006 |
| WO | WO-03/005918 A1 | 1/2003 |
| WO | WO-2006/102124 A2 | 9/2006 |
| WO | WO-2006/102124 A3 | 9/2006 |
| WO | WO-2010/098809 A2 | 9/2010 |
| WO | WO-2010/098809 A3 | 9/2010 |

* cited by examiner

SINGLE INSTRUMENT ELECTROSURGERY APPARATUS AND ITS METHOD OF USE

FIELD OF THE INVENTION

This invention relates to electrosurgery generally and more specifically to an electrosurgical instrument.

BACKGROUND

Electrosurgery is a well known technology utilizing an applied electric current to cut, ablate or coagulate human or animal tissue. See U.S. Pat. No. 7,789,879 issued to Daniel V. Palanker et al., incorporated herein in its entirety by reference. Typical electrosurgical devices apply an electrical potential difference or a voltage difference between a cutting electrode and a portion of the patient's grounded body in a monopolar arrangement or between a cutting electrode and a return electrode in bipolar arrangement, to deliver electrical energy to the operative field where tissue is to be treated. The voltage is applied as a continuous train of high frequency pulses, typically in the RF (radio frequency) range.

The operating conditions of electrosurgical devices vary, see the above-referenced patent, in particular a configuration of the cutting electrode is described there whereby a conductive liquid medium surrounding the electrode is heated by the applied electric current to produce a vapor cavity around the cutting portion of the electrode and to ionize a gas inside a vapor cavity to produce a plasma. The presence of the plasma maintains electrical conductivity between the electrodes. The voltage applied between the electrodes is modulated in pulses having a modulation format selected to minimize the size of the vapor cavity, the rate of formation of vapor cavity and heat diffusion into the material as the material is cut with an edge of the cutting portion of the cutting electrode.

The operating principle thereby is based on formation of a thin layer of a plasma along the cutting portion of the cutting electrode. Typically some sort of conductive medium, such as saline solution or normally present bodily fluids, surround the cutting portion of the electrode such that the liquid medium is heated to produce a vapor cavity around the cutting portion. During heating an amount of the medium is vaporized to produce a gas inside a vapor cavity. Since typically the medium is saline solution or bodily fluids, the gas is composed primarily of water vapor. The layer of gas is ionized in the strong electric field or on the cutting electrode to make up the thin layer of plasma. Because the plasma is electrically conductive, it maintains electrical conductivity.

The energizing electrical energy modulation format in that patent includes pulses having a pulse duration in the range of 10 microseconds to 10 milliseconds. Preferably the pulses are composed of minipulses having a minipulse duration in the range of 0.1 to 10 microseconds and an interval ranging from 0.1 to 10 microseconds between the minipulses. Preferably the minipulse duration is selected in the range substantially between 0.2 and 5 microseconds and the interval between them is shorter than a lifetime of the vapor cavity. The peak power of the minipulses can be varied from minipulse to minipulse. Alternately, the minipulses are made up of micropulses where each micropulse has a duration of 0.1 to 1 microsecond.

Preferably the minipulses have alternating polarity, that is exhibit alternating positive and negative polarities. This modulation format limits the amount of charge transferred to the tissue and avoids various adverse tissue reactions such as muscle contractions and electroporation. Additional devices for preventing charge transfer to the biological tissue can be employed in combination with this modulation format or separately when the method is applied in performing electrosurgery. This pulsing regime is not limiting.

Typically the temperature of the cutting portion of the electrode is maintained between 40 and 1,000° C.

That patent also describes particular shapes of the electrode and especially its cutting portion in terms of shape and dimensionality. Such electrosurgical devices provide several surgical techniques, including cutting, bleeding control (coagulation) and tissue ablation. Typically different types of electrodes and energizing formats are used for various purposes since the amount of energy applied and the type of tissue being worked on differ depending on the surgical technique being used.

Further, it is known in the field for a single electrosurgery hand piece to have detachable electrodes, such as for instance a cutting electrode and a coagulation electrode. At any one time, only a single electrode is attached to the hand piece, see U.S. Pat. No. 5,984,918 issued to Garito et al. where multiple sized electrosurgical electrodes are connected to a handle using a collet member.

Therefore a known technical problem is that during a surgical procedure, the surgeon must switch between various types of electrosurgical equipment, at least by changing the electrode type. This is typically done by swapping between various electrodes either by changing the electrode portion applied to the body as in Garito et al., or by using entirely different sets of equipment for cutting and coagulation or ablation.

It has been found by the present inventors that this is undesirable and a better system would provide several types of surgical techniques using a single electrosurgical apparatus.

SUMMARY

An apparatus for electrosurgery in accordance with the invention has been found to reduce operating time, increase ease of use of the equipment, and combine several surgical techniques in one device, including especially cutting and coagulation. In surgery, typically cutting of tissue in the operative field is followed by coagulation of the remaining tissue in the resulting wound to prevent bleeding. Coagulation generally refers to heating the tissue surface so as to seal off small severed blood vessels that would otherwise leak blood into the wound. Coagulation is necessary to prevent blood loss and also because blood leaking into the wound obscures the surgeon's view of the operative field.

The present electrosurgical apparatus provides what is referred to as single instrument surgery and carries out both precision resection (cutting) as well as enhanced coagulation (bleeding control). A typical use is in transcolation, for joint replacement surgery. In some embodiments, this apparatus includes an integrated feature to suck out blood, fluids, smoke, etc. from the operative field to keep the operative field clear, or to supply fluid such as saline solution to the operative field.

In one embodiment the present apparatus includes a hand unit which is mostly conventional for grasping by the surgeon, and which is conventionally coupled at its proximal portion by an electric cable to a control unit which provides the energizing electric pulses or current. The hand unit includes controls including at least one switch or button. The hand unit terminates at its distal portion in a conventional electrosurgical blade (electrode) which is intended for a first electrosurgical procedure such as the cutting (dissection) of tissue, thereby forming the primary assembly. In one embodiment, this electrode is a conventionally shaped electrosurgical blade intended for cutting soft tissue and is typically of metal most of the surface area of which is electrically insulated such as by a thin layer of glass.

The type of electrical energy applied to this blade by the control unit is, e.g., as described in the above-referenced patent so as to provide plasma type conditions at the electrode tip for tissue cutting, but this is not limiting. In one embodiment, this blade has a 3.0 mm wide spatula shaped tip mounted on a variable length (extendable) shaft. An example is in the PEAK PlasmaBlade® 3.05 surgical instrument supplied by PEAK Surgical, Inc., of Palo Alto, Ca. which has a telescoping electrode shaft and a spatula shaped electrode tip which is 3 mm wide, and an integrated aspiration feature. This device includes the hand unit.

In one embodiment, the present apparatus is a monopolar type cutting device (like the PEAK PlasmaBlade instrument) whereby the return current path is via a grounding pad or other return electrode affixed to the patient's body remote from the electrosurgical instrument. In other embodiments, the present apparatus is a bipolar type where the return electrode is located on or near the main electrode and is an integral part of the electrosurgical apparatus, as also well known in the field.

The secondary assembly of the present apparatus, in one embodiment, is intended for a second electrosurgical procedure such as tissue coagulation. It terminates at its distal portion in its own electrode blade or tip which in one case is hemispherical (ball shaped) and which is the distal end of an electrode shaft which is at least partially insulated. The proximate portion of the electrode shaft terminates in a housing which fits closely around the electrode shaft and provides heat and electrical insulation and a finger grip region. However, the housing itself is not intended to be held by the surgeon when the apparatus is in use. Instead, this housing fits snugly over the electrode blade of the primary assembly so that the electrode of the primary assembly also makes electrical contact with the electrode shaft of the secondary assembly. The electrical energy (pulsing) or continuous wave regime applied to the electrode of the secondary assembly (via the hand unit) may differ from that supplied to the primary assembly. The selection of the electrical energy regime is conventionally performed by the surgeon by manipulating controls on the control unit or on the hand unit For coagulation, the duty cycle regime of the applied electrical energy is, e.g., in the range of 12% to 19%. With associated peak to peak voltages in the range of 1300 to 5000 volts, the coagulation effect can be achieved using the electrode of the secondary assembly with conventional settings of the associated pulse generator of "cut", "coagulation" or "blend." Since the surface area of this coagulation electrode is large with respect to the applied voltage, the effect is resistive heating of the tissue rather than plasma generation that would ablate (cut) the tissue. For coagulation, generally the electrode is heated to about 100° C. so as to heat fluids in the tissue so the tissue in contact with the active portion of the electrode desiccates or stops bleeding:

When the secondary assembly is thus mounted to the primary assembly, the apparatus is suitable for coagulation since the primary assembly's electrode blade is now hidden and only serves as a mechanical mounting and electrical connection to the electrode of the coagulation (secondary) assembly. The secondary assembly fits over the distal portion of the primary assembly, e.g., with a snap (friction) fit so the secondary assembly can be readily attached and removed by the surgeon during surgery, without unscrewing or any tool. Thereby the surgeon can quickly switch between cutting and coagulation procedures, with essentially the same apparatus. When the surgeon mounts the coagulation (secondary) assembly to the primary assembly, he also may reset the control unit to supply electrical energy (pulsing or continuous) in the desired modulation regime suitable for tissue coagulation by the coagulation electrode.

In some embodiments, the two electrodes each carry a non-stick coating on their exposed (non insulated) portions. The coagulation electrode may be a ball, tube, screen, suction coagulator or forceps type electrode. Also the secondary (coagulation) assembly may be provided with a drip chamber near its distal portion or a perforated shaft so as to deliver fluid to the operative field, such as saline, or to provide aspiration. In some embodiments, a conventional channel or other type of passage such as a tube is provided for aspiration of smoke and/or fluid from the wound or fluid delivery. This passage (or passages) may be provided in only the secondary or primary assembly or in both in a fluid communication fashion. In some embodiments, the secondary assembly near its distal portion defines one or more aspiration ports, such as three such ports arranged around the circumference of the assembly and spaced at 120 degrees from one another, all in communication with the aspiration channel.

In one embodiment, the coagulation assembly's electrode shaft is bendable so that the surgeon can bend it and it remains in the bent position for ease of reaching portions of the operative field. The housing of the secondary assembly defines exterior finger grip ridges (ribs) in one embodiment so as to make it easier for the surgeon to attach and detach it from the primary assembly.

Therefore the secondary assembly, which in one embodiment is intended for coagulation, attaches to the primary assembly and by making electrical and mechanical contact thereto, conducts the electrical energy originating at the control unit, via the primary assembly electrode, to the tip of the coagulation assembly electrode. The shape of the electrode of the primary assembly is not limited to being a blade, but may take any other typical shape, such as a ball, tube, screen, suction coagulator or forceps. In one embodiment, the mechanical and electrical contact between the two assemblies is maintained at least partly by a spring in the housing of the secondary assembly.

Further, in other embodiments the functionality of the primary and secondary assemblies is reversed, so the primary electrode is for coagulation and the secondary electrode is for cutting. In other embodiments, the two electrodes have other intended uses in terms of electrosurgical procedures.

Advantages of the present device include reduced cost in use, since there is no need to supply saline solution to the operative field. This also reduces smoke production, making the surgery easier. Further there is no need for a separate aspiration device, since aspiration is integrated into the device.

DETAILED DESCRIPTION

Figure 1:
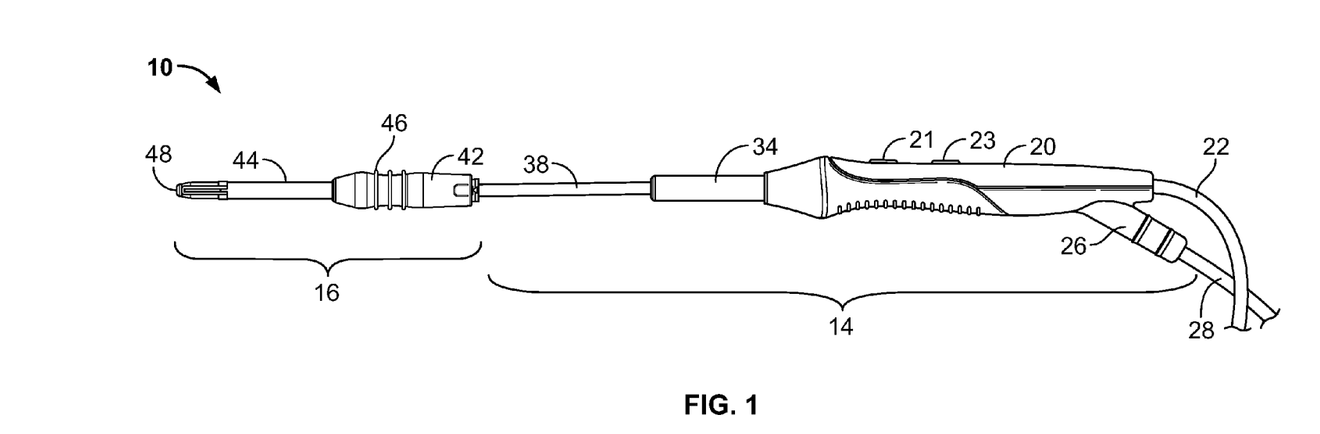
FIG. 1 shows an embodiment of the present apparatus as fully assembled, including the coagulation (secondary) assembly and the hand piece and electrode of the primary (main or cutting) assembly.

FIG. 1 shows an electrosurgical apparatus 10 in accordance with the invention, having two main portions or assemblies. Primary assembly 14 is intended for tissue cutting and includes a conventional hand piece 20 to which is conventionally coupled an insulated electrical cable 22 for providing the energizing electrical current or pulses. Also provided is extension 26 from which extends conventionally a tube or tubes for aspiration and/or providing fluid. These tubes are connected through suitable channels to a distal portion of the primary assembly. Also shown in FIG. 1 is the boot or seal 34 between the hand piece 20 and shaft 38; boot 34 is typically of electrically insulative material such as silicone, extending from which is the electrode shaft 38. Assembly 14 is, e.g., the PEAK PlasmaBlade device as described above. Conventional cut/coagulation control buttons are respectively at 21, 23.

The second portion of the apparatus 10 is the secondary (here a coagulation "cap") assembly 16 which includes housing 42 including exterior finger grip ridges 46, and from which extends an insulated shaft 44 terminating in electrode tip 48. Note that dimensions and materials here are largely conventional, as explained hereinafter.

Figure 2:
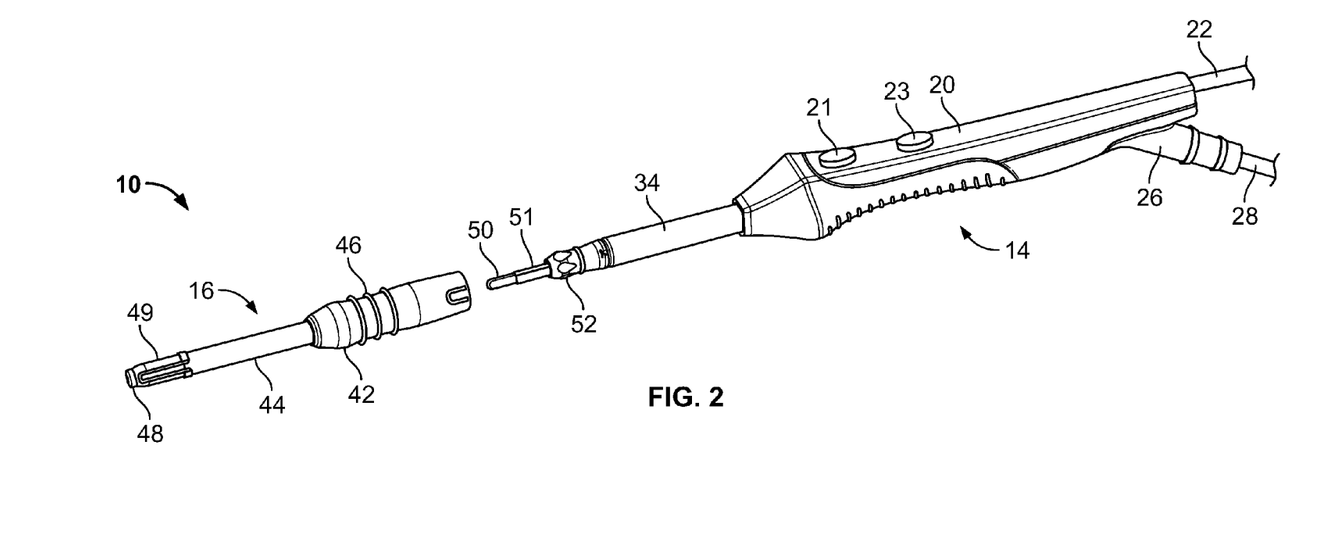
FIG. 2 shows the primary assembly separated from the coagulation assembly of FIG. 1.

FIG. 2 also shows the two assemblies 14 and 16 in a slightly different view, but detached (demounted) from one another. Generally the same reference numbers used in different figures here refer to the same or similar structures. In FIG. 2, extension portion 38 of the primary assembly is not visible since it is retracted.

In FIG. 2, since the two assemblies are shown detached, also visible is the base portion 52 of the primary assembly which in one embodiment has its own grip 52 as described and shown further below. Typically grip 52 is, e.g., of a high durometer (hard) polymer material. Blade 50 extends from an insulated portion 51.

In one embodiment, shaft 44 of secondary assembly 16 is bendable. While here assembly 16 has a hemispherical or ball electrode 48, this electrode may have any other shapes, such as tube, screen or forceps. Moreover, the exposed conductive (non-insulated) portion of electrode 48 may carry a non-stick coating, such as carbon with a protein such as a collagen, or a material such as PTFE or other flouro-polymer. This electrode is metal and glass coated, but the glass defines a large number of voids or micro-cracks which in use define hot spots by increasing the local impedance to the energizing electrical current. So these hot spots are intended to cause arcing and heating. A typical impedance is 50 to 2K ohms. While this glass insulation wears away as a result of the arcing, this is not problematic due to the use of this electrode for only one surgical procedure. A typical thickness of this glass layer is 0.003 to 0.007 inches (0.076 to 0.178 mm).

In one embodiment, the shaft of the coagulation electrode immediately proximal its tip 48 is surrounded by a drip chamber 49 for supplying fluid to the operative field, supplied via a suitable passage defined through secondary assembly 16 and connecting to a similar passage in the primary assembly 14. This passage and drip chamber provide, for instance, saline solution to the operative field.

Figure 3:
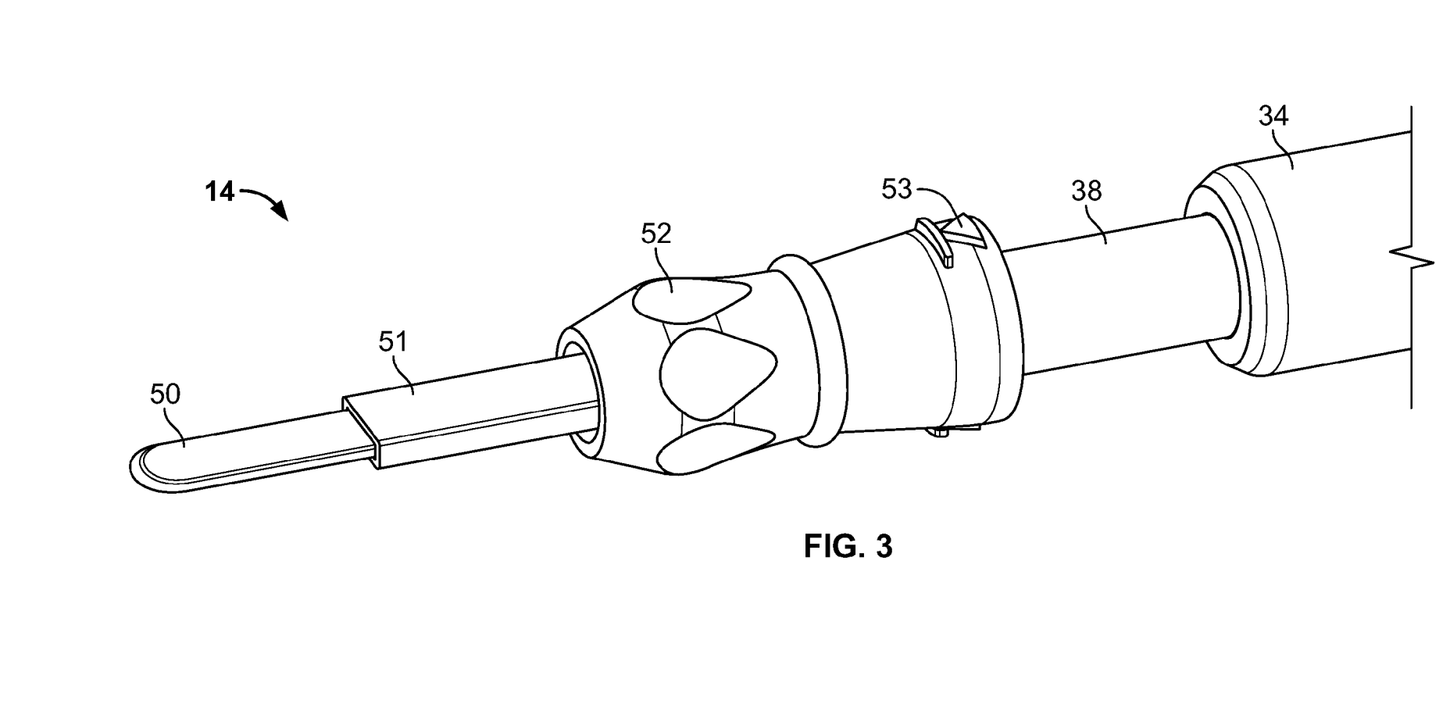
FIG. 3 shows the distal end of the primary assembly, including its cutting electrode.

FIG. 3 shows detail of the distal portion of the primary assembly 14, including similar structures as in FIGS. 1 and 2. FIG. 3 also shows in greater detail the grip 52. Arrow indicator 53 is provided so that the operator, such as a surgeon, has a reference indicator that the shaft 38 extends from the boot 34. Attachment of the secondary assembly 16 onto the primary assembly 14 is not orientation specific in this embodiment.

Figure 4:
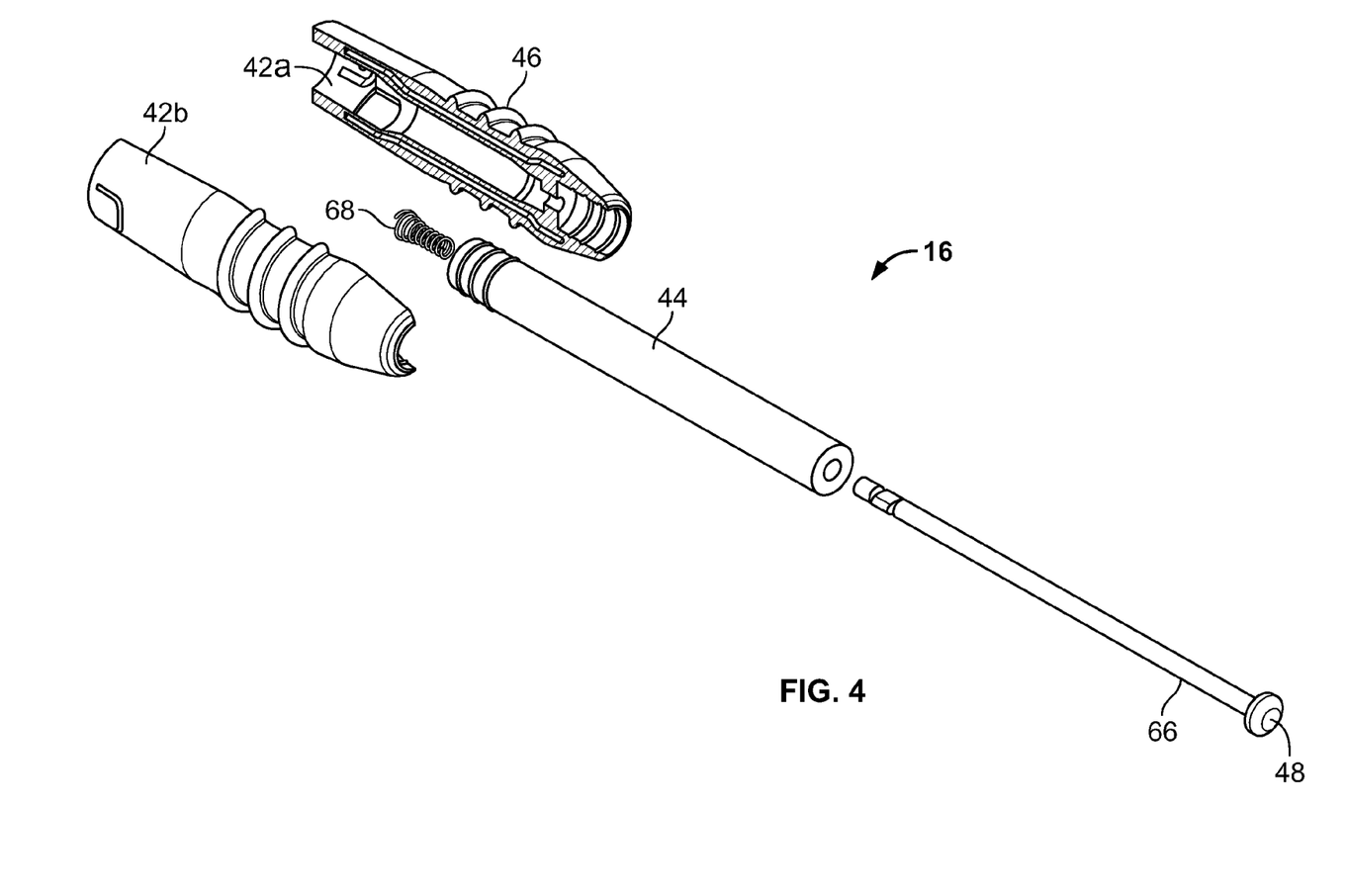
FIG. 4 shows an exploded view of the coagulation assembly.

FIG. 4 is an "exploded" view of the coagulation assembly 16. The ball tip 48 of the electrode is the distal portion of a conventional metal (or similar electrically conductive material) shaft 66 which can be bendable. The outer portion 44 of the shaft here is an electrically insulative tubing, such as plastic, which covers most of the length of conductive shaft 66. This tubing 44 may be perforated to deliver saline or serve as an aspiration channel for smoke. In other embodiments it is not so perforated. Spring 68 surrounds and contacts the proximal end of shaft 66, as explained hereinafter. Housing 42 includes two mating portions 42a and 42b, each for instance of plastic.

Figure 5:
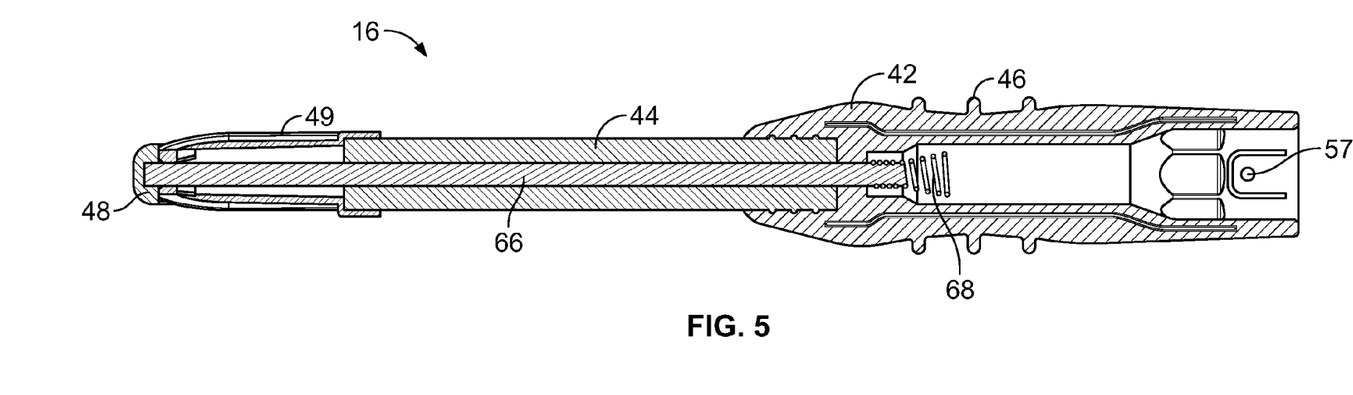
FIG. 5 shows detail of the coagulation assembly in a cross-sectional view.
Figure 6:
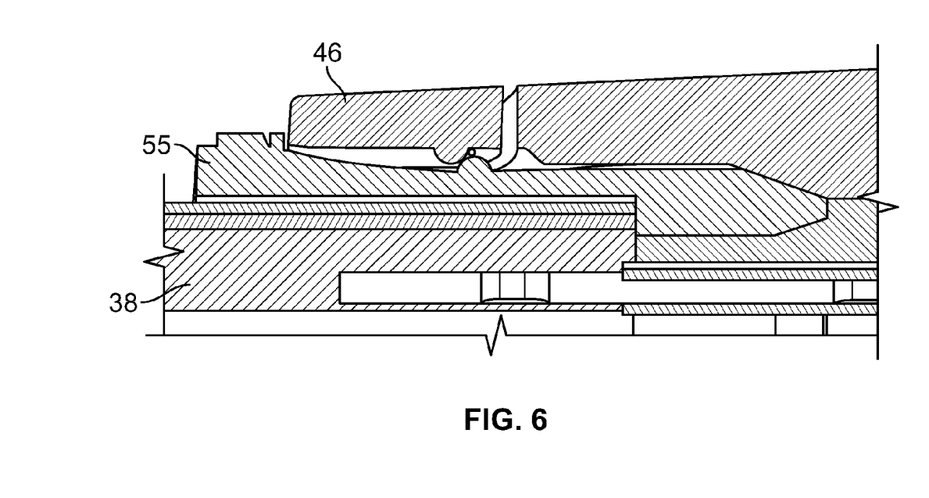
FIG. 6 shows detail of the tip of the coagulation assembly.

FIG. 5 shows a cross-sectional view of the coagulation assembly 16. FIG. 6 shows detail of the tip of the coagulation assembly 16. As shown, a short distance proximal from ball electrode 48, aspiration port 67 is defined in the shaft 66 and its outer portion 44, for passage of smoke, blood, etc. into an interior channel defined in shaft 66, in this embodiment. There are for instance three such ports disposed around shaft 66, equally spaced apart circumferentially. A typical diameter of the ball electrode is 0.18 inches (4 mm) and the port diameter is typically 0.06 inches (1.5 mm). The outer shaft 44 is electrically and heat insulative, for instance made of plastic, and is typically 0.10 inch (2.5 mm) thick. Some of this insulation extends into the port 67, to prevent debris build up in the port.

Figure 7:
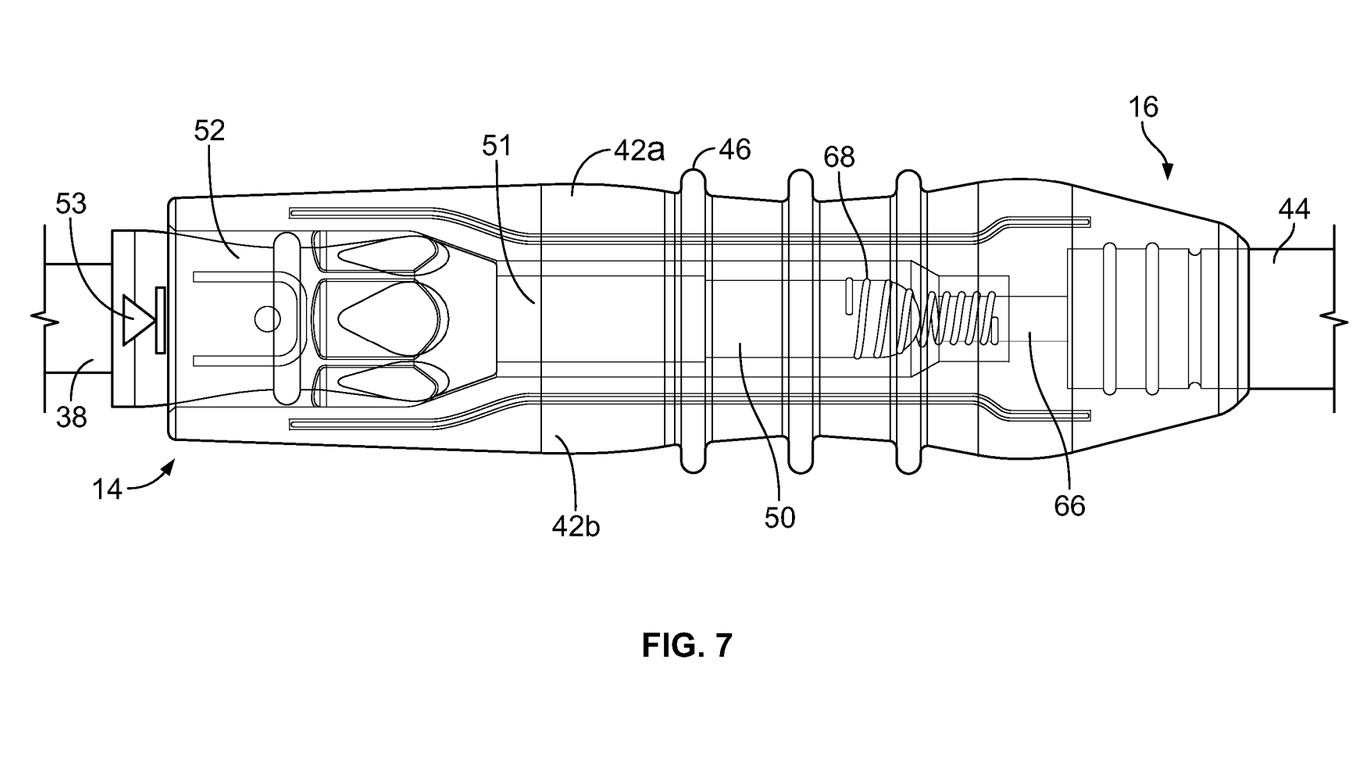
FIG. 7 shows an "X-ray" view of the distal end of the primary assembly and the proximal end of the coagulation assembly.

FIG. 7 shows in a "X-ray" view how primary assembly 14 mates with coagulation assembly 16. Again, the reference numbers refer to the same structures as in the other figures. The two housing halves 42a, 42b of the coagulation assembly fit over and engage the grip 52 of the primary assembly 14. The mating is intended to be finger tight so the two assemblies can be attached and detached with normal hand strength. Spring 68 of coagulation assembly 16 fits over and engages blade 50 of the primary assembly 14. Arrow indicator 53 on primary assembly 14 points to an associated indicator mark on the exterior of the coagulation assembly housing 42, as described above. The mating portions of the two assemblies in this embodiment are both rotatably symmetric, so there is no need to align one to the other rotationally.

Other portions of the present electrosurgical system which are conventional are not shown here. Notably the control unit provides the electric current or pulses as explained above and is of the type well known in the field and is electrically coupled via cable 22 to the present apparatus. An example of such a control unit is the PULSAR® Generator power supply supplied by PEAK Surgical, Inc.

Also provided, if needed, is a conventional source of fluid and/or a source of vacuum, for aspiration, as well known in the field. Typically the electrically non-conductive portions of the apparatus are polymer or plastic in terms of the housings, tubing, etc. and of conventional materials. The insulative tubing is typically heat shrink or silicone material. The two halves 42a, 42b of housing 42 are glued or otherwise fastened together, although in other embodiments, this housing is a single piece of material. As explained above, the coagulation assembly shaft 66 may be of a bendable material, such as a somewhat flexible or annealed metal rod such as, for instance, stainless steel and has a typical diameter of 0.5 to 2 mm.

Typically the two electrodes are single use (disposable) so as to be used for only a single surgical operation. In particular the entire coagulation subassembly 16 is typically disposable. In terms of the primary assembly 14, the entire assembly is also disposable, or at least its distal portions including the electrode and its shaft are disposable and detachable from the hand piece which then may be reusable.

As described above, the exposed (non-insulated) electrode tips of both the primary assembly and the coagulation assembly in one embodiment carry a non-stick coating. These coatings in one embodiment are conventional polymers or flouropolymers. In another embodiment they are diamond like carbon which conventionally is one of several forms of an amorphous carbon material formed by deposition.

In other embodiments, the electrode tip coatings are carbon together with a collagen or other protein. For instance this coating may be carbon graphite with a protein or albumin binder. The thickness of the carbon coating on the metal (or other conductive material) surface of the electrode, as needed to support an electrical discharge, is in the range of 10 μm to 1 mm. Conventional carbon sputtering provides only a thickness of 0.1 μm, which is inadequate. A pyrolitic carbon deposition method is known from Morrison, Jr. U.S. Pat. No. 4,074,718 incorporated herein by reference in its entirety, forming carbon on an electrode by burning carbohydrate-containing materials deposited on the electrode.

The present coating process is different and first involves providing a mixture of carbon or graphite powder (of any convenient particle size) and a binder. The mixture is 1% to 50% powdered carbon or graphite (by weight or volume), preferably about 30% by volume. The binder is a solution of a protein or similar material such as albumin, gelatin, collagen or other biocompatible material in water or other solvent. For instance, the binder may be a 35% solution by volume of albumin in saline solution.

The bare electrode is briefly dipped into the mixture. The coated electrode is then air dried for, e.g., one minute to one hour at an ambient temperature of 200° C. to 300° C., or until all the solvent has evaporated. Then the coated electrode is placed in an oven for a few seconds to an hour, at a temperature of 200° C. to 600° C. E.g., this baking step takes 5 minutes at 300° C. (Note that the drying and baking can be combined into one step.)

The electrode is then cooled in the air and ready for assembly with the associated components of the apparatus.

This disclosure is illustrative and not limiting. Further modifications will be apparent to those skilled in the art in light of this disclosure, and are intended to fall within the scope of the appended claims.

We claim:

1. Apparatus for electrosurgery comprising:
   a primary assembly including:
      a hand unit;
      a first shaft extending from the hand unit and terminating in a first electrode adapted to perform a first procedure on tissue; and
   a secondary assembly including:
      a housing;
      a second shaft extending from the housing and terminating in a second electrode adapted to perform a second procedure on tissue;
   wherein the housing is detachably mountable on the first electrode and the first shaft, and when the housing is mounted on the first electrode and the first shaft, the second electrode is electrically coupled to the first electrode.

2. The apparatus of claim 1, further comprising a spring within the housing, wherein when the housing is mounted to the first electrode, the spring engages the first electrode.

3. The apparatus of claim 1, wherein the second shaft is flexible.

4. The apparatus of claim 1, further comprising a chamber disposed around at least a portion of the second shaft and in fluid communication with the hand unit when the housing is mounted, the chamber defining a plurality of ports.

5. The apparatus of claim 1, wherein the second shaft defines an interior cavity which is in fluid communication with the hand unit when the housing is mounted, and further defines a plurality of ports in fluid communication with the cavity.

6. The apparatus of claim 1, wherein an exterior surface of the housing carries at least one rib.

7. The apparatus of claim 1, wherein the second electrode is one of a ball, tube, screen, or forceps type.

8. The apparatus of claim 1, further comprising a portion of the first shaft defining a plurality of flat surfaces, and wherein an interior of the housing mates with the flat surfaces.

9. The apparatus of claim 1, wherein at least a portion of the first or second electrode carries insulation.

10. The apparatus of claim 9, wherein a portion of the first or second electrode not carrying the insulation carries a layer of carbon and a protein.

11. The apparatus of claim 10, wherein the layer has a thickness greater than or equal to 10 μm.

12. The apparatus of claim 1, wherein the first shaft is extendable in length from the hand unit.

13. The apparatus of claim 1, wherein the first and second procedures are selected from the group consisting of: cutting, coagulating, ablating, and desiccating.

14. A method of performing surgery, comprising the acts of:
   providing a primary assembly including a hand unit and a first shaft extending from the hand unit and terminating in a first electrode adapted to perform a first procedure on tissue;
   performing the first procedure on tissue with the first electrode;
   providing a secondary assembly including a housing and a second shaft extending from the housing and terminating in a second electrode adapted to perform a second procedure on tissue;
   wherein the housing is detachably mountable on the first electrode and the first shaft;
   mounting the housing on the first electrode and first shaft, wherein when so mounted, the second electrode is electrically coupled to the first electrode; and
   performing the second procedure on tissue with the second electrode.

15. The method of claim 14, wherein the first and second procedures are selected from the group consisting of: cutting, coagulating, ablating and desiccating.

* * * * *